US008029994B2

(12) United States Patent
Aoki et al.

(10) Patent No.: US 8,029,994 B2
(45) Date of Patent: Oct. 4, 2011

(54) METHOD OF IDENTIFYING A TARGET ANALYTE USING PHOTONIC CRYSTAL RESONATORS, AND RELATED DEVICE

(75) Inventors: Kanna Aoki, Saitama (JP); Massimo De Vittorio, Lecce (IT); Tiziana Stomeo, Martano (IT); Ferruccio Pisanello, Paris (FR); Alessandro Massaro, Ancona (IT); Luigi Martiradonna, Bari (IT); Stefania Sabella, Galatina (IT); Rosaria Rinaldi, Lecce (IT); Yasuhiko Arakawa, Kawasaki (JP); Roberto Cingolani, Lecce (IT); Pier Paolo Pompa, Lecce (IT)

(73) Assignee: Consiglio Nazionale Delle Ricerche-INFM Istituto Nazion, Genoa (IT)

(*) Notice: Subject to any disclaimer, the term of this patent is extended or adjusted under 35 U.S.C. 154(b) by 9 days.

(21) Appl. No.: 12/534,266

(22) Filed: Aug. 3, 2009

(65) Prior Publication Data

US 2010/0028898 A1 Feb. 4, 2010

(30) Foreign Application Priority Data

Aug. 4, 2008 (IT) .............................. TO2008A0614

(51) Int. Cl.
*C12Q 1/68* (2006.01)
*G01N 33/53* (2006.01)
*C12M 1/00* (2006.01)
(52) U.S. Cl. ......... 435/6; 435/7.1; 435/283.1; 536/23.1; 536/24.3
(58) Field of Classification Search .................. 435/4, 6, 435/7.1, 283.1
See application file for complete search history.

(56) References Cited

U.S. PATENT DOCUMENTS

| 6,096,496 | A | 8/2000 | Frankel |
| 6,777,244 | B2 | 8/2004 | Pepper et al. |
| 6,990,259 | B2 | 1/2006 | Cunningham |
| 7,206,488 | B1 | 4/2007 | Altug et al. |
| 2002/0182716 | A1 | 12/2002 | Weisbuch et al. |
| 2006/0209413 | A1 | 9/2006 | Kim et al. |
| 2007/0252981 | A1 | 11/2007 | Spillane et al. |
| 2010/0087011 | A1* | 4/2010 | Cooper .......................... 436/501 |
| 2010/0088039 | A1* | 4/2010 | Yang et al. ...................... 702/23 |
| 2010/0119193 | A1* | 5/2010 | Englund et al. ................. 385/16 |
| 2010/0163410 | A1* | 7/2010 | Mastromatteo et al. ....... 204/400 |

FOREIGN PATENT DOCUMENTS

WO WO89/09937 * 10/1989

OTHER PUBLICATIONS

Bizet et al., Validation of antibody-based recognition by piezoelectric transducers through electroacoustic admittance analysis. Biosensors & Bioelectronics 13 (3-4) : 259-269 (1998).*
Bizet at., Immunodetection by quartz crystal microbalance Applied Biochemistry and Biotechnology. vol. 89, 2000.*
Godber et al. Direct Quantification of Analyte Concentration by Resonant Acoustic Profiling. Clinical Chemistry 51(10) : 1962-1972 (2005).*
Yuan et al., Bond rupture of biomolecular interactions by resonant quartz crystal. Analytical Chemistry 79 : 9039-9044 (2007).*
Ringler, M, et al.; "Shaping Emission Spectra of Fluorescent Molecules With Single Plasmonic Nanoresonators"; Physical Review Letters American Physical Society USA; vol. 100, No. 20, May 23, 2008; pp. 203002-1, XP002562360; ISSN: 0031-9007.
Italian Search Report dated Apr. 17, 2009 corresponding to Italian Application No. TO20080614.
Dawson, J.M., et al., GaN Photonic Crystal-Based, Enhanced Fluorescence Biomolecule Detection System, Mater. Res. Soc. Symp. Proc. (2008), pp. 1040-Q09-29, vol. 1040, XP002524054.
Mathias, P., et al., Graded Wavelength One-Dimensional Photonic Crystal Reveals Spectral Characteristics of Enhanced Fluorescence, Journal of Applied Physics, American Institute of Physics., May 12, 2008, vol. 103, No. 9, pp. 94320-94320, New York, US, XP012110813.
Akahane, Y., et al., High Q Photonic Nanocavity in a Two Dimensional Photonic Crystal, Nature (2003), pp. 944-947, vol. 425.
Bodovitz, S., et al., Protein Biochips: The Calm Before the Storm, DDT., Feb. 2005, pp. 283-287, vol. 10 No. 4.
Cheng Jing, et al., Analysis of Ligase Chain Reaction Products Amplified in a Silicon-Glass Chip Using Capillary Electrophoresis, Journal of Chromatography A, (1996), pp. 151-158, vol. 732.
Cockerill, F.R., Application of Rapid-Cycle Real-Time Polymerase Chain Reaction for Diagnostic Testing in the Clinical Microbiology Laboratory, Arch Pathol Lab Med, Sep. 2003, pp. 1112-1120, vol. 127.
Daniel, J.H., Silicon Microchambers for DNA Amplification, Sensors and Actuators A, (1998), pp. 81-88, vol. 71.

(Continued)

*Primary Examiner* — Ethan C Whisenant
(74) *Attorney, Agent, or Firm* — Sughrue Mion, PLLC

(57) ABSTRACT

A method of identifying target analytes in a sample, particularly a biological sample, comprising the steps of putting a plurality of target analytes, bound to a common luminescent marker, in contact with a plurality of molecular probes immobilized on a support, each of said molecular probes being capable of complementary binding to a respective target analyte, if said target analyte is present in the sample, providing to said support an excitation radiation and detecting an emission radiation coming from said support as a result of at least one complementary binding event, characterized by the fact that:
said support comprises a plurality of photonic crystal resonators, at least two of said resonators being characterized by different resonance wavelengths;
each of said molecular probes being fixed to a respective resonator; and by the fact that
the identification of at least one target analyte is carried out through the analysis of the total emission spectrum coming from said plurality of photonic crystals resonators, in order to detect possible wavelength resonance peaks generated as a result of the binding of said target analyte, bound to the common luminescent marker, to one or more of said molecular probes.

6 Claims, 3 Drawing Sheets

OTHER PUBLICATIONS

Domiati-Saad, R., et al., Nucleic Acid Testing for Viral Burden and Viral Genotyping, Clinica Chimica Acta (2006) pp. 197-205, vol. 363.

Dunn, W.C., et al., PCR Amplification and Analysis of Simple Sequence Length Polymorphisms in Mouse DNA Using a Single Microchip Device, Analytical Biochemistry (2000), pp. 157-160, vol. 277.

Fan, J.B., et al., Highly Parallel Genomic Assays, Aug. 2006, pp. 632-644, vol. 7.

Ferguson, J. A., et al., A Fiber-Optic DNA Biosensor Microarray for the Analysis of Gene Expression, Nature Biotechnology, Dec. 1996, pp. 1681-1684, vol. 14.

Foresi, J.S. et al., Photonic-Bandgap Microcavities in Optical Waveguides, Nature, Nov. 13, 1997, pp. 143-145, vol. 390.

Ganesh, N., et al., Enhanced Fluorescence Emission From Quantum Dots on a Photonic Crystal Surface, Nature Nanotechnology, Aug. 2007, pp. 515-520, vol. 2.

Hadd, A.G., et al., Microchip Device for Performing Enzyme Assays, Analytical Chemistry, Sep. 1, 1997, pp. 3407-3412, vol. 69, No. 17.

Happ, T.D., et al., Nanofabrication of Two-Dimensional Photonic Crystal Mirrors for 1.5 μm Short Cavity Lasers, Journal of Vac Science & Technology, Nov./Dec. 2001, pp. 2775-2778, vol. 19 No. 6.

Joannopoulos, J.D., et al., Photonic Crystals—Molding the Flow of Light, 1995, pp. 4-137, Princeton University Press.

Johnson, S., et al., Linear Waveguides in Photonic-Crystal Slabs, Physical Review, Sep. 15, 2000-II, pp. 8212-8222, vol. 62, No. 12.

Kopp, Martin U., et al., Chemical Amplification: Continuous-Flow PCR on a Chip, Science, 1998, pp. 1046-1048 (1998), vol. 280.

Mathias, P.C., et al., Combined Enhanced Fluorescence and Label-Free Biomolecular Detection With a Photonic Crystal Surface, Applied Optics, Apr. 20, 2007, pp. 2351-2360, vol. 46, No. 12.

Mekis A. et al., High Transmission Through Sharp Bends in Photonic Crystal Waveguides, Physical Review Letters, Oct. 28, 1996, pp. 3787-3790, vol. 77, No. 18.

Murphy, Lindy, Biosensors and Bioelectrochemistry, Current Opinion in Chemical Biology, (2006), pp. 177-184, vol. 10.

Piunno, Paul A.E., et al., Fiber-Optic DNA Sensor for Fluorometric Nucleic Acid Determination, Analytical Chemistry vol. 67 No. 15, Aug. 1, 1995, pp. 2635-2643, vol. 67, No. 15.

Scherer, J. R., et al., Ultra-High Throughput Rotary Capillary Array Electrophoresis Scanner for Fluorescent DNA Sequencing and Analysis, Electrophoresis, (1999), pp. 1508-1517, vol. 20. No. 7.

Scully, M. O., et al., Quantum Optics, 1997, 002-630, Cambridge University Press, Cambridge.

Song, Bong-Shik, et al., Ultra-High-Q Photonic Double-Heterostructure Nanocavity, Nature Materials, Mar. 2005, pp. 207-210, vol. 4.

Speers, D. J., et al., Clinical Applications of Molecular Biology for Infectious Diseases, Clin Biochem Rev, Feb. 2006, pp. 39-51, vol. 27.

Yablonovitch, E., Inhibited Spontaneous Emission in Solid-State Physics and Electronics, Physical Review Letters, May 18, 1987, pp. 2059-2062, vol. 58, No. 20.

Wang, J., Survey and Summary From DNA Biosensors to Gene Chips, Nucleic Acids Research, (2000), pp. 3011-3016, vol. 28, No. 16.

Wang, Joseph, Electrochemical Enzyme Immunoassays on Microchip Platforms, Analytical Chemistry, Nov. 1, 2001, pp. 5323-5327, vol. 73, No. 21.

Wong, M. L., et al., Real-Time PCR for mRNA Quantitation, BioTechniques (Jul. 2005), pp. 75-85, vol. 39, No. 1.

* cited by examiner (a)

(b)

METHOD OF IDENTIFYING A TARGET ANALYTE USING PHOTONIC CRYSTAL RESONATORS, AND RELATED DEVICE

The present invention regards a method and a device for identifying an analyte, particularly a biomolecule present in a biological sample, and finds application in genomic, proteomic and in bio-chip manufacturing.

The development of micro- and nano-manufacturing technologies, associated to biomolecular modelling and micro-electromechanical systems (MEMS), has considerably contributed to the creation of miniaturized laboratories applied to genomic and proteomic analysis. The application fields of these miniaturized laboratories are extremely broad, and they have been referred as bio-chip and also other terms such as gene-chip, gene-array, DNA microarray, protein chip, and lab-on-chip. Basically these chips, developed both in simple, stand-alone configuration and in integrated structures/devices, are planar structures, obtained on several substrates such as glass or plastic materials, whereon (bio)molecule probes (such as DNA, proteins or cells, which selectively recognize target molecules) are immobilized through chemical surface modification or through in situ synthesis [Fan, 2006]. These chips can be made of suitable micro-reactors and/or capillary systems and apparatus for the detection of the (bio)recognition/reaction among the biomolecular species in solution.

The biochip technology has deeply changed the field of molecular biology, particularly in genomic and proteomic, in experimental and clinical diagnostic and in pharma-genomic, finding applications such as enzyme assays, immunochemistry assays, detection of genetic polymorphisms, sequencing of nucleic acids and DNA amplification on micro-volumetric scale.

In particular, due to the high specificity of the hybridisation reaction among oligonucleotide sequences, chips based on biomolecular interactions among DNA strands have been developed more rapidly than chips based on proteins. In the latter case, despite the keen interest among the scientific community, the development has been slowed down by the complex bio-recognition mechanism of proteinaceous molecular species.

In general, the binding between a (bio)molecule and a target specie must be expressed as a detectable and measurable signal. The detection mechanism can use several physical phenomena such as light emission, electrochemical response and variations in electric potential, mass, current or frequency. Among these options, the optical detection is the most widely spread analysis method. The optical detection method is essentially based on the measurement of luminescence originating from a luminescent marker associated to a pair of complementary molecules (e.g. complementary oligonucleotides), formed by the target analyte and the (bio) molecular probe.

Typically, the luminescent marker is conjugated to the target analyte under examination, and the emitted signal is detected after the interaction (biorecognition) between target and probe molecules (e.g. afterward a hybridisation reaction). During the detection process of the signal, the read-out region is properly illuminated by an excitation light and a detector collects the optical signal emitted by the marker. These approaches, although give only qualitative information on an analyte in the sample, nevertheless are extremely effective, since they can screen a large number of different biomolecules with a single chip. The probe species, or biorecognition elements, with known (nucleotide) base sequences, are immobilized at predetermined positions of the chip, having for instance a typical matrix configuration. At light emission coming from a predetermined coordinate of the matrix, a specific nucleotidic sequence of the captured analyte is rapidly associated. Recently, several solutions exploiting photonic crystals for the optical read-out area of biochips have been proposed. Photonic crystals, thanks to their periodic variation of the refractive index in one, two or three directions (1D, 2D, or 3D), permit to design the photonic modes and to obtain high-reflective mirrors [Happ, 2001], waveguides [Mekis, 1996; Johnson, 2000] and micro- or nano-optical resonators [Foresi, 1997; Akahane, 2003; Song, 2005].

Such approaches can be classified as a function of the use or not of luminescent markers.

In "label-free" detection methods, no luminescent markers are associated to the target analytes. Instead, the variation of the resonant wavelength of photonic crystal resonators caused by the presence of target analytes caught onto the surface (for instance, hybridised DNA) is detected. The analytes locally modify the refraction index of the upper cladding layer on the photonic crystal, shifting its resonance frequency. The detection of these spectral shifts is performed by reflectance or transmittance measurements on a single resonator [Pepper, 2004; Cunningham, 2006; Altug, 2007]. Therefore, the analysis of the read-out region is performed through a multiple sequential scanning of the whole read-out area, single resonator by single resonator.

U.S. Pat. No. 6,990,259 shows the manufacturing of photonic crystal cells, arranged in matrices, wherein "defects" in the periodic structure have been inserted. Such defects induce a localized increase of the intensity of the electromagnetic field determining:

a) the increase of Q factor (index of the spectral width of the optical mode resonating in the defect),
b) the increase of the sensor sensitivity thanks to the interaction of the sample with an increased fraction of electromagnetic energy, exactly localized at the point where the same sample is placed.

Such device works on "label-free" methods and moreover allows a quantitative measurement of the analyte; the interaction with the sample determines the spectral shift of the wavelength resonating peak of the reflected or transmitted light through the photonic crystal, and the amount of such shift is a function of the analyte concentration.

The other approach is based on the analyte detection though the luminescence of markers conjugated to the same analyte. Particularly, using photonic crystal resonators produce a significant increase in the emission of fluorophores. In this case, the electromagnetic field corresponding to the excitation wavelengths is locally increased by properly designing resonant or leaky modes [Ganesh, 2007; Mathias, 2007]. This approach in based on the increase of the whole spectrum of fluorescence, without performing any selective enhancement at specific frequency. The ratio between the useful signal and the noise coming from diffusion or reflection of the excitation light is significantly increased, nevertheless it is always necessary to perform a sequential scanning of the whole chip (matrix of photonic crystal resonator).

Notwithstanding these improved approaches, the need of developing novel detection methods with higher precision and higher-speed analysis is still required.

In particular, the object of the invention is to provide a new method and a new optical device based on the combination of the photonic crystal technology with the nano-biotechnologies useful to improve the current solutions in terms of detection sensitivity, signal-to-noise ratio and speed of the read-out method.

In view of such, object of the present invention are a method and a device as defined in the following claims.

In the appended drawings:

FIGS. 2a and 2b are schematic representations showing a phase of the using method of the optical device (bio-chip) according to the invention, referring respectively to the binding event between:

Figure 3:
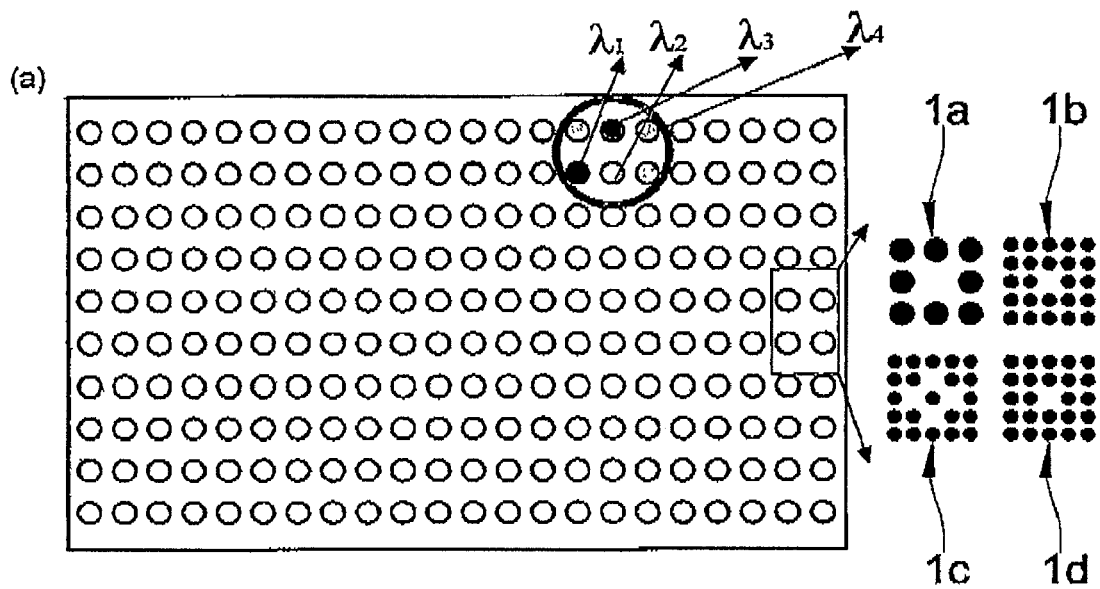
Figure 3:
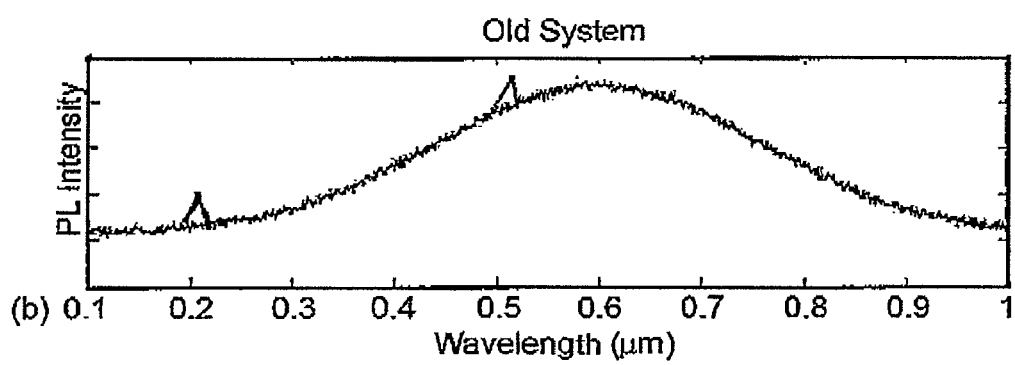
Figure 3:
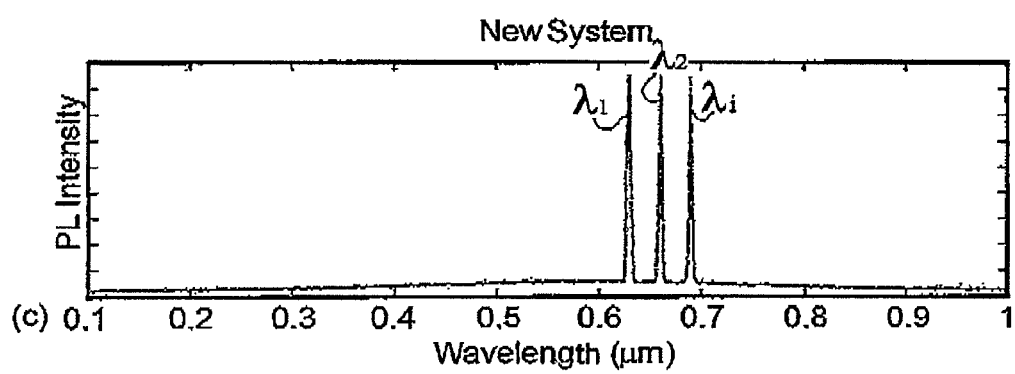

a) a bio-recognition element (probe) for a specific analyte (target) under examination (oligonucleotides, proteins, ligands) and b) a DNA sequence (target) under examination which binds to a specific probe formed by a complementary molecule (sequence) of ssDNA;

FIG. 3a is a scheme of a matrix of photonic crystal resonators used in the optical device according to the invention;

FIG. 3b shows a typical example of emission spectrum collected from a read-out area, not assisted by photonic crystal resonators; and FIG. 3c shows an example of the spectrum of the emission signal detected on the whole read-out area of an optical device according to the invention.

According to the invention, the photonic crystal technology is applied to the optical read-out region of the biochip (bio-recognition region), wherein the excitation and the emission of the luminescent markers conjugated with the analyte or analytes under examination takes place. These analytes, as already explained, interact specifically and selectively with the bio-recognition elements, immobilised on the resonator surface.

The device for detecting the optical signal comprises a substrate, whereon a matrix of photonic crystal resonators is formed. 1D, 2D, and 3D geometries with linear or non-linear materials can be used for manufacturing of micro- or nano-optical resonators (regions where the light, trapped, is then emitted in the vertical direction only at specific frequencies or optical modes). Photonic crystals are able to control the light propagation, introducing a 1D, 2D or 3D periodicity in materials showing a high optical transparency in the frequency range of interest.

Micro- or nanocavities made by photonic crystal resonating in the emission spectral band of a luminescent marker are used.

In particular, using 2D photonic crystals (which can be easily integrated in planar structures), these resonators can be manufactured in a waveguide formed on a substrate having a different refraction index or on a suspended guiding layer in a membrane configuration.

The detecting device could have a final configuration similar to the previously cited bio-chip devices currently used, with a chamber intended for receiving the solution containing the assay to analyse and having a wall formed by the substrate on which the matrix of photonic crystal resonators is obtained. The final device can have high mechanical robustness, by using, for instance, photonic crystals resonators made on a silicon layer, suspended in air (membrane), or grown on silicon dioxide layer, or titanium dioxide layer over silicon dioxide, or a silicon nitride ($Si_xN_y$) membrane or silicon nitride over silicon dioxide, or gallium arsenide (GaAs) over aluminium gallium arsenide ($Al_xGa_{1-x}As$); an high flexibility can be obtained by using a membrane structure made of Poly-methilmethacrilate (PMMA) or PMMA on Poly-DiMethilSiloxane (PDMS).

Preferably, at least two photonic crystal resonators of the photonic crystal matrix have different resonant wavelengths and more preferably each photonic crystal resonator shows an own distinct resonant wavelength.

Figure 1:
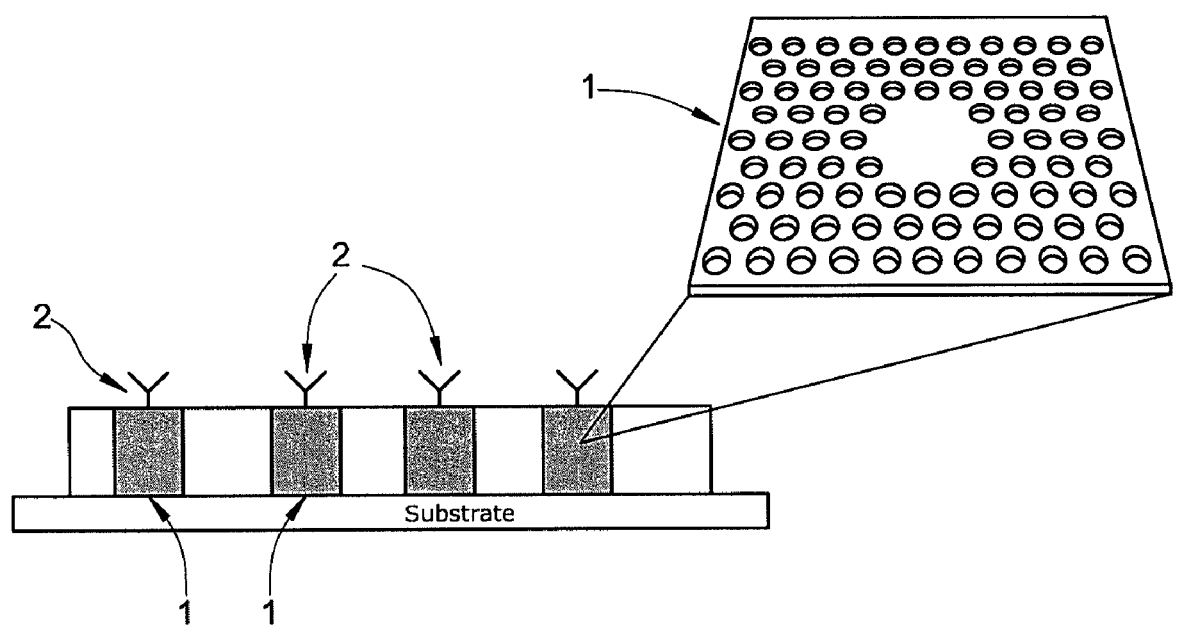
FIG. 1 is a scheme of an optical device for the biomolecular analysis, according to the invention.

On the surface of each resonator, specific probes for the analytes to detect, such as single-stranded DNA (ssDNA) sequences, antibodies, receptors, aptamers and alike, are fixed. In FIG. 1, by way of an example, matrices of photonic crystals 1 and probe biomolecules 2 of the same typology are represented. Obviously, different photonic crystal structures having different resonant wavelengths can be contemplated inside the same matrix of the chip and, similarly, each biorecognition probe, uniquely bound to a single resonator structure, can be different from the others and characteristic for each analyte.

The probes 2 are bound with high spatial precision by means of chemical, physical or electrostatic techniques.

Figure 2:
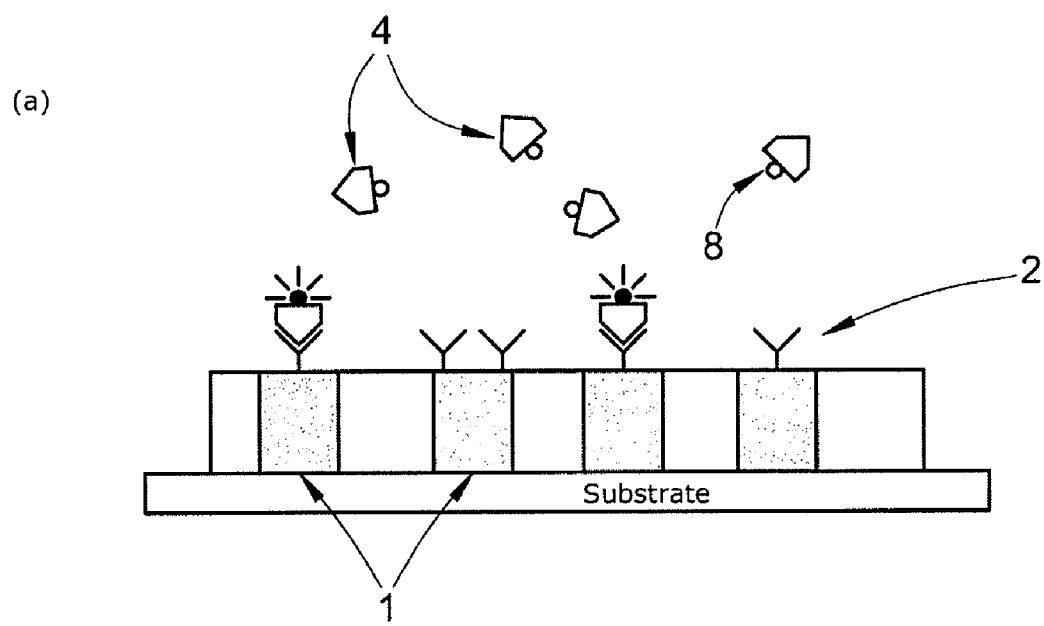
Figure 2:
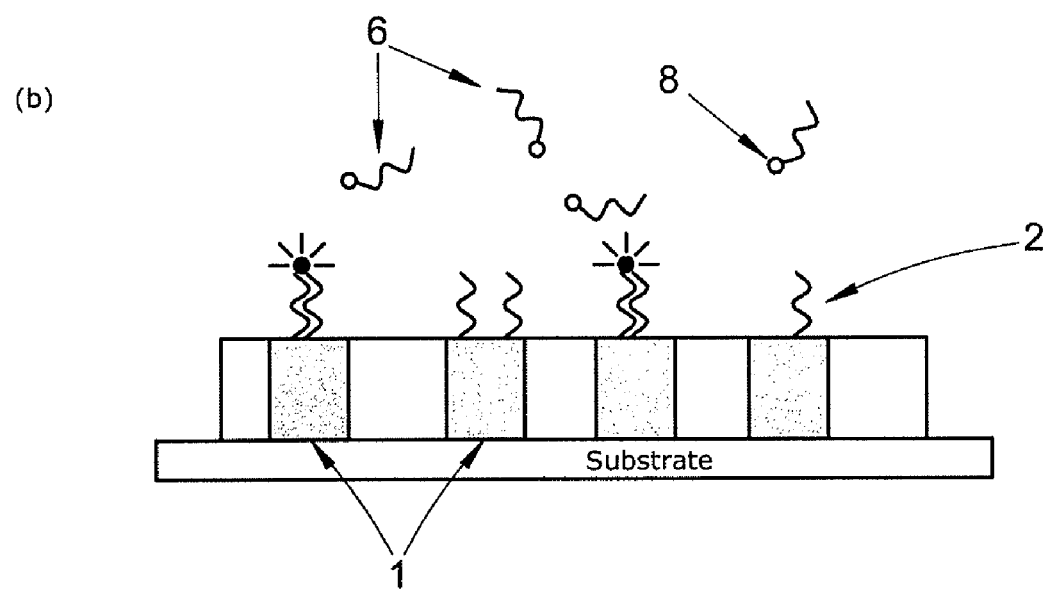

The basic scheme for detecting biomolecules 4 (proteins, ligands, and alike.) and nucleic acids 6 is respectively shown in FIGS. 2a and 2b. Referring also to the scheme in FIGS. 2a and 2b, the resonators can differ each other, as well as the biorecognition elements 2 bound to each resonator.

Target analytes 4,6 are directly (e.g. by synthesis) or indirectly marked through conjugation with a sole luminescent marker, typically a fluorophore, common to all the target analytes 4,6. Alternatively, multiple markers can be used for the purpose of increasing analysis procedures executed in parallel.

The device subject of the invention is based on a unique and original detection scheme. The detection is carried out collecting the emission spectrum coming from the whole biorecognition area of the chip. By applying a suitable matrix composed by photonic crystal resonators having different resonant wavelengths, each biorecognition element of the device is unambiguously associated to a different resonance peak. By analysing the emission spectrum, it is possible to identify such resonant peak and therefore to get back to the presence of specific target (bio)molecules analytes 4,6 contained in the analysed sample.

Thus, it is possible in a single analysis run to collect at the same time the signals coming from several resonators, by increasing the speed of the signal collection and elaboration. Moreover, the photonic crystals strongly inhibits the excitation radiation diffused or reflected towards the detection direction. The elimination of such diffused or reflected radiation, together with the enhancement of the intensity of the emission signal coming from the resonators, significantly increases the overall signal-to-noise ratio. This feature permits to reduce the reading errors, allowing the operators to avoid the following and complex step of post-processing and correction of the collected data. In order to further decrease the background noise, caused by the scattering of the excitation light, such excitation light can be selectively addressed toward the read-out region by means of optical waveguides.

By the way of an example, 2D photonic crystal resonators made of silicon nitride ($Si_xN_y$) suspended membranes are considered. A sole common fluorophore with broad emission spectral band in the visible range is employed. Such fluorophore is used to mark all target analytes 4,6 contained in the analysed assay. In order to obtain resonant structures in the visible spectral band, a periodic bidimensional grating, comprising circular holes with a diameter of about 100 nm and a period of about 300 nm, is made in the silicon nitride membrane (having a thickness of about 400 nm). In such periodic grating, a periodicity defect is introduced in order to obtain the resonant region (e.g. by removing or modifying the dimensions of one of the holes made in the periodic grating). Said bidimensional periodic grating having a periodicity defect represents a resonator characterised by a resonant wavelength $\lambda_i$, being itself the $i^{th}$ element of a matrix of resonators as illustrated in FIG. 3a.

A predefined bio-recognition element 2 is univocally associated to the $i^{th}$ resonator, and therefore a resonating condition at wavelength $\lambda_i$ is univocally associated to said element. If the target analyte 4,6 corresponding to the predefined bio-recognition element 2 is present in the analysed assay, it will specifically bind to such element; as a consequence, the broad-band fluorophore used to mark the target analytes 4,6 will be affected by the specific resonating effect of the $i^{th}$ resonator, thus modifying in a predefined way its emission with an increment of its intensity at the wavelength $\lambda_i$.

FIG. 3b shows a typical example of the emission signal collected from a read-out area, not assisted by photonic crystal resonators. The curve shape is typical of the original marker, and includes a significant noise due to scattered excitation light.

FIG. 3c is an example of an emission spectrum detected on the whole read-out area, where $\lambda_1$, $\lambda_2$ and $\lambda_i$ are the light wavelengths emitted by the luminescent markers as a consequence of the binding between the target analytes 4,6 with the probes 2 associated to said resonators. The presence of each peak in the overall spectrum reveals therefore the presence of the corresponding target analyte 4,6 in the analysed assay.

According to the invention, the photonic crystals technology can therefore be applied to biochip technology in order to provide the following advantages:
a) controllability of the resonant wavelength of each resonator in the matrix through an accurate choice of the materials and their design; specifically, it becomes possible to enhance the intensity of the emission spectrum of the fluorophore conjugated to an analyte: this allows to perform an optical detection based not only on a spatial discrimination of the different contributions but also on a spectral discrimination, since each pixel corresponds to a specific optical resonator working at a defined frequency (FIG. 3a).
b) increasing of the intensity of fluorophore emission at specific spectral bands, thus enhancing the signal-to-noise ratio.
c) possibility to selectively excite the luminescent marker via waveguides or a resonance of a certain optical mode in the photonic crystal for suppressing the light diffused, reflected or diffracted by the substrate: this can be achieved by controlling the emission or excitation angle by a proper design of the photonic crystal; this propriety can be exploited to spatially separate the excitation radiation from the emission radiation.

Regarding point (a), an external excitation light addressed towards the matrix at a proper angle will excite the marker bound to the captured analyte, which will emit its typical broad-band signal. Then, the broad-band signal is amplified by the photonic crystal resonator in specific spectral bands (FIG. 3a). In such figure, four embodiments of photonic crystal resonators 1a-1d are illustrated. The variation from pixel to pixel (i.e. from analyte to analyte) of the frequencies contemporarily emitted from the matrix allows a high degree of parallelism over a high number of different analytes, thus speeding up the recognition of the examined samples.

Regarding points (b) and (c), the proper choice of both materials and geometry of the photonic crystals can lead to the creation of a spectral energy band-gap that suppresses the intensity of the electromagnetic signal propagating towards specific directions. By creating defects in the photonic crystal, it is possible to localize specific optical modes inside said spectral band-gap, whose intensity is selectively amplified in specific directions.

Further advantages of the invention comprise:
the possibility to obtain the proposed detection system, based on spectral discrimination (spectral multiplexing), also in a system based on spatial distinction;
increasing of the data acquisition speed through the spectral analysis of the signal coming from the whole read-out area;
unambiguous association of a certain emission spectrum to each analyte contained in an unknown assay, by using a sole marker common for all the analytes, or two or multiple markers. The use of multiple markers is not carried out for the purpose of assigning a spectral peculiarity to target analytes previously bonded to the bio-recognition element, but for the purpose of increasing the overall spectral emission width of the employed markers, with as a further result the enhancement of the in parallel analysis procedures;
high spectral resolution in detection, by using photonic crystal resonators with high quality-factor;
possibility to develop more complex photonic crystal structures for coupling the resonant peak signals with guided and leaky modes in the photonic crystal pattern, to efficaciously transport the excitation light and/or the emission signals from the read-out areas to the detector.

Naturally, the principle of the invention remaining the same, the embodiments and details of construction may be widely varied with respect to those described above and illustrated purely by way of a non-limiting example, without thereby departing from the scope of protection of the present invention, defined in the appended claims.

BIBLIOGRAFIA

Akahane, Y., Asano, T., Song, B.-S., and Noda, S., *Nature*, 425, 944-947 (2003).
Altug, H., and Vuckovic, J., U.S. Pat. No. 7,206,488, Apr. 17, 2007.
Bodovitz, S., Joos, T., and Bachmann, *J. DDT* 10 (4), 283-287 (2005).
Cheng, J., Shoffner, M. A., Mitchelson, K. R., Kricka, L. J., and Wilding, P., *J. Chrom. A* 732 (1), 151-158 (1996).
Cockerill, F. R., *Arch. Pathos. Lab. Med.* 127, 1112-1120 (2003).
Cunningham, B. T., U.S. Pat. No. 6,990,259 B2, Jan. 24, 2006.
Daniel, J. H et al., *Sensors and Actuators A: Physical*, 71 (1-2), 81-88 (1998).
Domiati-Saad, R., and Scheuermann, R. H., *Clinica Chimica Acta* 363 (1-2), 197-205 (2006).
Dunn, W. C. et al., *Anal. Biochem.* 277 (1), 157-160 (2000).
Fan, J.-B., Chee, M. S., and Gunderson K. L., *Nature Review Genetics* 7, 632-644 (2006).
Ferguson, J. A., Boles, T. C., Adams, C. P., and Walt, D. R., *Nature Biotech.* 14 (13), 1681-1684 (1996).
Foresi, J. S. et al., *Nature* 390, 143-145 (1997).
Ganesh, N. et al., *Nature Nanotechnology* 2, 515-520 (2007).
Hadd, A. G. et al., *Anal. Chem.* 69 (17), 3407-3412 (1997).
Happ, T. D. et al., *Journal of Vacuum Science & Technology B* 19(6), 2775-2778 (2001).
Joannopoulos, J. D., Meade, R. D., and Winn, J. N., *Photonic Crystals—Molding the Flow of Light*, Princeton University Press, Princeton, 1995.
Johnson, S. G., Villeneuve, P. R., Fan, S., and Joannopoulos, J. D., *Phys. Rev. B* 62, 8212-8222 (2000).
Kopp, M. U., de Mello, A. J., and Manz, A., *Science* 280 (5366), 1046-1048 (1998).
Mathias, P. C., Ganesh, N., Chen, L. L., and Cunningham, B. T., *Appl. Opt.* 46, 2351-2360 (2007).

Mekis, A. et al., *Phys. Rev. Lett.* 77, 3787-3790 (1996).
Murphy, L., *Current Opinion in Chemical Biology* 10, 177-184 (2006).
Pepper, D. M., and Sievenpiper, D., U.S. Pat. No. 6,777,244, Aug. 17, 2004.
Pae, P., Uj, K., Rhe, H. et al., *Analytical Chemistry* 67(15), 2635-2643 (1995).
Scherer, J. R. et al. *Electrophoresis* 20(7), 1508-1517 (1999).
Scully, M. O., and, Zubairy, M. S., *Quantum Optics*, Cambridge University press, Cambridge, 1997.
Song, B.-S., Noda, S., Asano, T., and Akahane, Y., *Nature Materials* 4, 207-210 (2005)
Speers, D. J., *Clin Biochem.* 27, 39-51 (2006).
Yablonovitch, E., *Phys. Rev. Lett.* 58, 2059-2062 (1987).
Wang, J., *Nucleic Acid Research* 28(16), 3011-3016 (2002).
Wang, J., Ibanez, A., Chatrathi, M. P., and Escarpa, A., *Anal Chem.* 73, 5323-5327 (2001).
Wrong, M. L., and Mediano, J. F., *BioTechniques* 39, 75-85 (2005).

What is claimed is:

1. A method of identifying target analytes in a sample, comprising the steps of:
   putting a plurality of target analytes, bound to a common luminescent marker, in contact with a plurality of molecular probes immobilized on a support, each of said molecular probes being capable of complementary binding to a respective target analyte, if said target analyte is present in the sample;
   providing to said support an excitation radiation and detecting an emission radiation coming from said support as a result of at least one complementary binding event, wherein:
   said support comprises a plurality of photonic crystal resonators, at least two of said resonators being characterized by different resonance wavelengths;
   each of said molecular probes being fixed to a respective resonator; and
   the identification of at least one target analyte is carried out through the analysis of the total emission spectrum coming from said plurality of photonic crystals resonators, in order to detect possible wavelength resonance peaks generated as a result of the binding of said target analyte, bound to the common luminescent marker, to one or more of said molecular probes.

2. The method according to claim 1, wherein the excitation radiation is provided through a waveguide.

3. The method according to claim 1, wherein the emitted radiation coming from the support is extracted through a waveguide.

4. The method according to claim 1, further comprising the step of localizing a predetermined optical mode of the excitation radiation in a defect region of the photonic crystal and enhancing the emitted radiation by coupling said emitted radiation with said optical mode.

5. A device for identifying a target analyte in a sample, the device comprising a plurality of molecular probes immobilized on a support, wherein at least one of said molecular probes is capable of complementary binding to said target analyte, if present in the sample, wherein:
   said support comprises a plurality of photonic crystal resonators, at least two of said resonators being characterized by different resonance wavelengths; and
   each of said molecular probes being fixed on a respective resonator.

6. A system for identifying a target analyte in a sample, comprising:
   a device according to claim 5;
   a source, arranged to provide to said device an excitation radiation;
   detection means arranged to acquire an emission radiation coming from said device, as a result of the complementary binding event; and
   calculation means associated to said device and arranged to analyse the total emission spectrum coming from the plurality of said photonic crystal resonators in order to detect possible wavelength resonance peaks generated as a result of the binding of said target analyte, bound to a luminescent marker, to one or more of said molecular probes.

* * * * *